US00PP09576P

United States Patent [19]

Glenn

[11] Patent Number: Plant 9,576

[45] Date of Patent: Jun. 11, 1996

[54] TRIDENT MAPLE TREE NAMED 'ABTIR'

[76] Inventor: Michael M. Glenn, 785 Cleveland Rd., Bogart, Ga. 30622

[21] Appl. No.: 417,157

[22] Filed: Apr. 3, 1995

[51] Int. Cl.[6] ..... A01H 5/00

[52] U.S. Cl. ..... Plt./53.6

[58] Field of Search ..... Plt./53.6

*Primary Examiner*—James R. Feyrer

*Attorney, Agent, or Firm*—Klarquist Sparkman Campbell Leigh & Whinston

[57] ABSTRACT

A new and distinct variety of trident maple (*Acer buergeranum*) named 'Abtir' characterized by (1) rapid growth; (2) early exfoliating bark; (3) lustrous dark green summer foliage; (4) and superb grayed-purple fall foliage.

2 Drawing Sheets

BACKGROUND OF THE INVENTION

The present invention comprises a new and distinct variety of trident maple (*Acer buergeranum*), referred to by the varietal name 'Abtir'.

The parent tree of the new variety was discovered in a nursery in Athens, Ga., among a group of random open-pollinated trident maple seedlings growing from seed collected in Decatur, Ga. This group of seedlings was grown as liners then transplanted to field spacing.

Trident maple seedling trees are extremely variable in growth habit, leaf, and bark characteristics. Seedling-grown material is often open and unkempt, characteristics that typically limit the attractiveness of the plants in landscaping applications.

The parent tree was observed to have superb grayed-purple colored fall foliage and exhibited multi-colored grayed-orange exfoliating bark. The trunk developed an attractive irregular fluted shape. The parent tree grew at a rapid rate, yet maintained a dense framework of branches and leaves, resulting from the more closely spaced nodes and greater multiple breaks from the new shoot growth of the season.

This invention has not been observed under all possible environmental conditions. However, the following combination of traits have been repeatedly observed in asexually propagated progeny and are determined to be the basic characteristics of this invention, which in combination distinguish this variety of trident maple as a new and distinct variety: (1) rapid growth; (2) early exfoliating bark; (3) lustrous dark green summer foliage; (4) and superb grayed-purple fall foliage. The new variety is readily identified as trident maple by the uniformity of these characteristics. To the inventor's knowledge, this combination of characteristics distinguish this new variety from all other varieties of trident maple of which I am aware.

Asexual reproduction of this new variety has initially and subsequently been accomplished at my direction in Oconee County, Ga. Firm-wood, four to six inch long cuttings were treated with 10,000 ppm naphtheneacetic acid dissolved in 50% alcohol. The cuttings were placed in horticultural grade perlite in four inch deep flats on a greenhouse bench under intermittent mist. Rooting occurred in six to ten weeks at a 40% to 60% success rate. The above-mentioned unique features are stable and reproduce true to type in each successive propagation.

Figure 1:
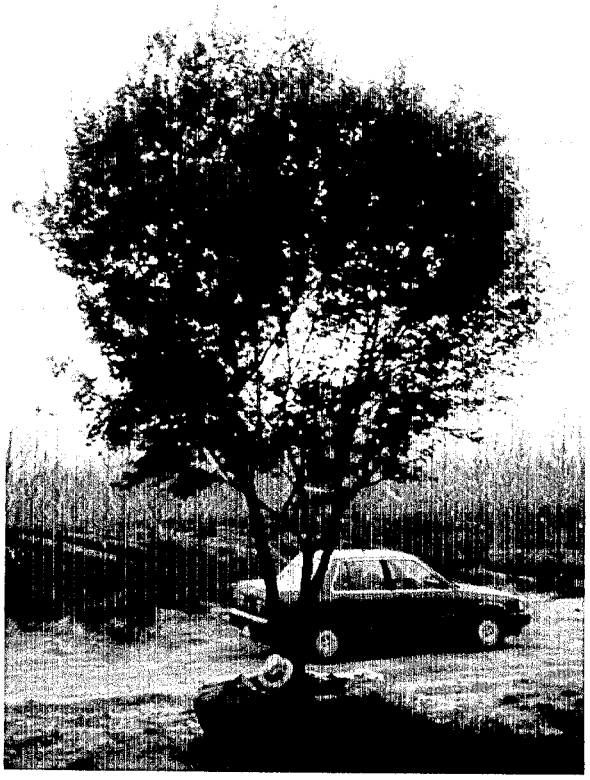
FIG. 1 is a photograph showing the 'Abtir' trident maple with summer foliage.
Figure 2:
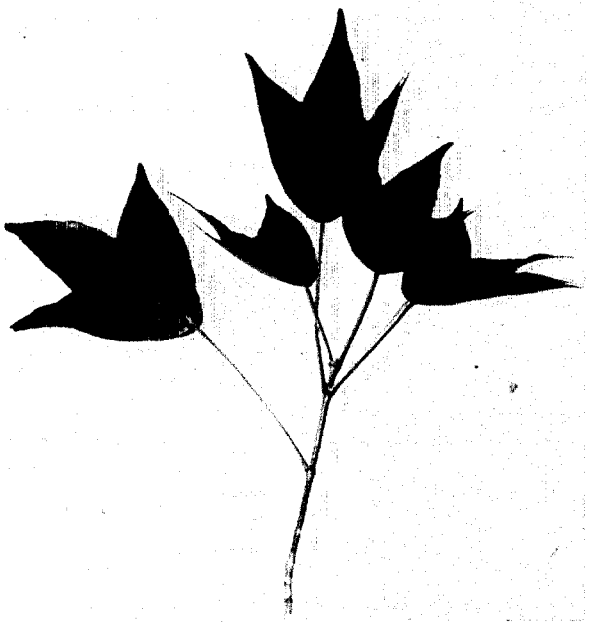
FIG. 2 is a photograph showing a branch of the new variety with summer foliage and illustrating the internodal spacing and typical branching characteristics of the variety.
Figure 3:
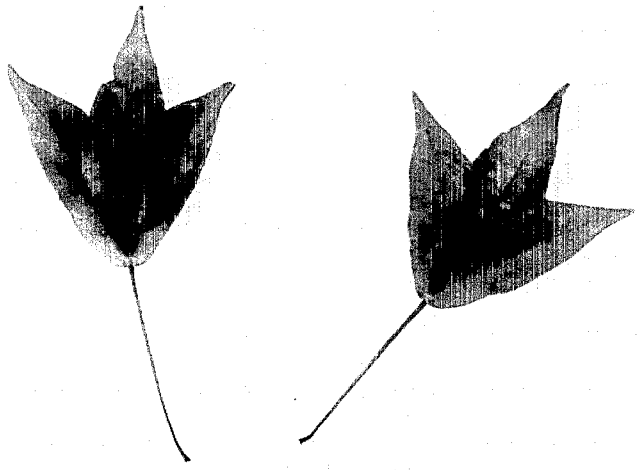
FIG. 3 is a photograph showing a branch of the new variety with fall foliage.
Figure 4:
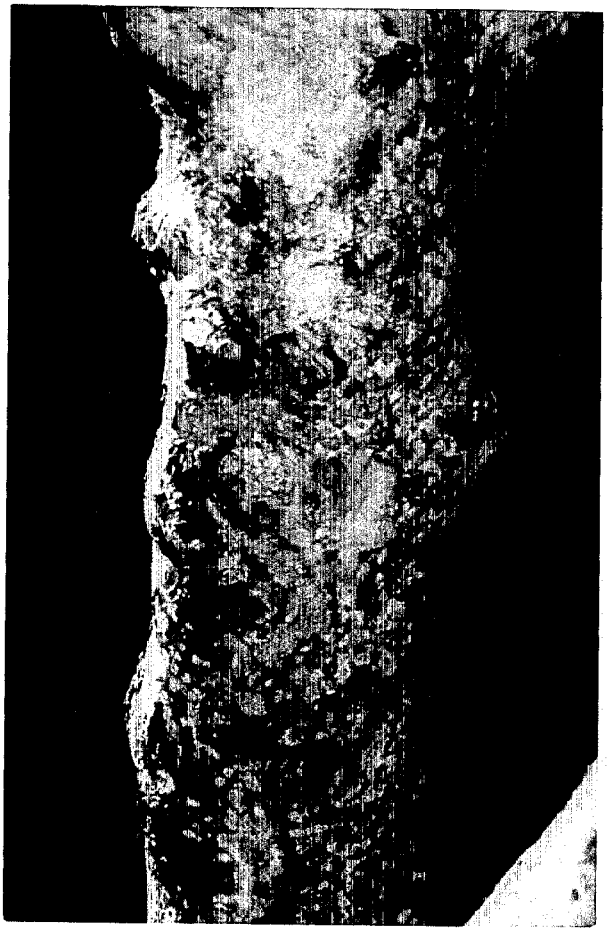
FIG. 4 is a close-up photograph showing in greater detail the exfoliating bark of the new variety.

These photographs were taken in April, 1993 (FIG. 1) in the field and in August, 1994 (FIGS. 2 and 4) and November, 1994 (FIG. 3) in a studio and illustrate typical characteristics of the new variety as noted, with color being as true as is reasonably possible to make the same in this type of color photograph.

DETAILED DESCRIPTION

The following is a detailed description of the invention based on plants growing and observed in Bogart, Ga. Color references are made to the Royal Horticultural Society Colour Chart (RHS), except where the context indicates a term having its ordinary dictionary meaning. All trident maple trees of the new variety, insofar as I have been able to observe them, have been identical in all the characteristics described below. Other than as set forth below, as of this time I have not observed any other characteristics which are different from seedling trident maple trees.

Parentage: Seedling of unknown parentage.

Propagation: Holds to distinguishing characteristics through succeeding propagation by rooted cuttings.

Locality where grown and observed: Bogart, Ga.

Tree: The parent plant reached 18 feet high after eight years. The height-to-width ratio of the parent tree and of asexually propagated progeny thereof is approximately 1.5. The branching habit and dendritic pattern is multiple-stemmed with three equal sized leaders. The secondary branches ascend at a 30–45 degree angle, producing an oval-rounded outline. Trunk diameter at six inches from the ground averages 7.25 inches. Internode length ranges from 0.5 to 2 inches, which produces the dense foliage canopy. The trunk develops a fluted character and the parent plant has an almost rectilinear outline in cross-section, being 8.5 inches long on two axes and 6 inches wide on the shorter axes.

Vigor: Vigorous, growing rapidly, particularly under nursery conditions. Although it grows on an average about 20 percent faster than other trident maple seedlings under the same conditions, the new tree maintains a dense framework of branches and leaves due to the more closely spaced internodes (and thus leaves) and greater multiple breaks from the new shoot growth of the season.

Foliage:

*Size.*—Leaves average 1.5 to 3 inches wide and high, average for the species.

*Shape.*—The mature leaf is tri-lobed and rounded. The lobes are triangular.

*Apex.*—Acute.

*Base.*—Broad cuneate form.

*Margin.*—Entire or slightly serrate.

*Color.*—The upper leaf surface is lustrous dark green (RHS 139A), slightly darker green than is typical for the species, and the lower surface is green (RHS 137C). Fall coloration is one of the unique attributes of this variety, since most trident maples do not develop reliable or spectacular autumnal coloration. In the location in which these observations were made, the coloration of fall foliage is grayed-purple (RHS 185A) and lasts for about two weeks.

*Petiole.*—Approximately as long as the blade.

Flowers and fruits:

*Size.*—Flowers and fruits are typical for the species, as are stems and buds.

*Other characteristics of flowers and fruits.*—Insofar as they have been observed, the flowers and fruits of the new variety are typical for the species.

Bark: Exfoliates at an early age (four years old), exposing a grayed-orange (RHS 173B to 177B) bark.

Ultimate tree size: Unknown at this time, although original tree reached 18 feet high after eight years.

I claim:

1. A new and distinct variety of trident maple substantially as herein shown and described.

* * * * *